(12) United States Patent
Broten et al.

(10) Patent No.: US 6,410,554 B1
(45) Date of Patent: Jun. 25, 2002

(54) COMBINATION THERAPY FOR THE TREATMENT OF BENIGN PROSTATIC HYPERPLASIA

(75) Inventors: Theodore P. Broten, Ambler; Peter K. S. Siegl, Blue Bell; Steven A. Nichtberger, Gladwyne, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/274,839

(22) Filed: Mar. 23, 1999

Related U.S. Application Data

(60) Provisional application No. 60/079,041, filed on Mar. 23, 1998.

(51) Int. Cl.[7] .................. A61K 31/44; A61K 31/505
(52) U.S. Cl. ............................. 514/299; 514/274
(58) Field of Search ................ 514/279, 299, 514/256, 274

(56) References Cited

U.S. PATENT DOCUMENTS

| | | |
|---|---|---|
| 4,703,063 A | 10/1987 | Imai et al. |
| 5,292,740 A | 3/1994 | Burri et al. |
| 5,387,603 A | 2/1995 | Kitazawa et al. |
| 5,389,620 A | 2/1995 | Ishikawa et al. |
| 5,389,629 A | 2/1995 | Shutske et al. ............. 514/217 |
| 5,403,842 A | 4/1995 | Leonardi et al. |
| 5,403,847 A | 4/1995 | Gluchowski et al. ....... 514/318 |
| 5,597,823 A | 1/1997 | Meyer et al. |

FOREIGN PATENT DOCUMENTS

| | | |
|---|---|---|
| EP | 0 617 001 A1 | 9/1994 |
| EP | 0 714 897 A1 | 5/1996 |
| WO | WO 94/25013 | 11/1994 |
| WO | PCT 96/04905 | 2/1996 |
| WO | WO 96/06095 | 2/1996 |
| WO | PCT 96/08487 | 3/1996 |
| WO | WO 96/14846 | 5/1996 |
| WO | PCT 96/22978 | 8/1996 |
| WO | PCT 96/22992 | 8/1996 |
| WO | WO 97/30045 | 8/1997 |
| WO | WO 98/57641 | 12/1998 |

OTHER PUBLICATIONS

P. Langenstroer et al., "Endothelin–1 in the Human Prostate: Tissue Levels, Source of Production and Isometric Tension Studies", Journal of Urology, vol. 149, pp. 495–499, Aug. 1993.

G. Le Brun et al., "Identification of Endothelin Receptors in Normal and Hyperplasia Human Prostate Tissue", The Prostate, vol. 28, pp. 379–384 (1996).

C. Imajo et al., "Evaluation of the Effect of Endothelin–1 and Characterization . . . " Journal of Urology, vol. 158, pp. 253–257, Jul. 1997.

C. Forray et al., "The Alpha 1 Adrenergic Receptor that Mediates Smooth Muscle Contraction . . . ", Molewcular Pharmacology, vol. 45, pp. 703–708 (1994).

T. J. Christmas et al., "Alpha–adrenoceptor blockers in the treatment of benign prostatic hyperplasia", World Journal of Urology, vol. 9, pp. 36–40 (1991).

*Primary Examiner*—Theodore J. Criares
*Assistant Examiner*—J. Kim
(74) *Attorney, Agent, or Firm*—Baerbel R. Brown; Catherine D. Fitch; Kenneth R. Walton

(57) ABSTRACT

This invention relates to combination therapy for the treatment of benign prostatic hyperplasia comprising an alpha-1a antagonist and an endothelin antagonist. More specifically, the use of a selective alpha-1a adrenergic receptor antagonist in combination with a subtype non-selective endothelin antagonist provides relief of lower urinary tract symptoms in patients with symptomatic prostatism or benign prostatic hyperplasia. This combination therapy improves lower urinary tract symptoms including increasing urine flow rate, decreasing residual urine volume and improving overall obstructive and irritative symptoms in patients with benign prostatic hyperplasia or symptomatic prostatism.

7 Claims, No Drawings

COMBINATION THERAPY FOR THE TREATMENT OF BENIGN PROSTATIC HYPERPLASIA

This application claims the benefit of U.S. Provisional Application No. 60/079,041, filed Mar. 23, 1998, the contents of which is hereby incorporated by reference in its entirety.

FIELD OF THE INVENTION

The present invention provides combination therapy for the treatment of benign prostatic hyperplasia. More particularly, the combination comprises an alpha-1a adrenergic receptor antagonist with an endothelin antagonist, and optionally a 5a-reductase inhibitor, for relief of lower urinary tract symptoms in patients with symptomatic prostatism or benign prostatic hyperplasia.

BACKGROUND OF THE INVENTION

Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concomitantly, the increased noradrenergic innervation of the enlarged prostate leads to an increased adrenergic tone of the bladder neck and urethra, further restricting the flow of urine through the urethra.

Bladder outlet obstruction (BOO) in BPH patients results from a static component of increased prostatic mass which physically impinges on the urethra and a dynamic component of increased contractile tone of the prostatic-urethral smooth muscle. Standard treatment of BPH involves surgical or pharmacological intervention. Surgical intervention, either by removal of the prostate via radical prostatectomy or removing the prostatic adenoma via transurethral resection of the prostate alleviates both the static and dynamic components of BOO since the entire prostate or the majority of the prostatic smooth muscle is removed. Although these procedures result in the most marked improvement in symptoms, there is the possibility of mortality and morbidity since these are invasive surgical procedures. Many patients suffer incontinence and retrograde ejaculation as a consequence of these surgical procedures. Because of the chances for morbidity and mortality, these procedures are not optimum for patients with mild to moderate symptoms in a disease which is not life-threatening.

Pharmacological treatment with 5a-reductase inhibitors such as finasteride reduces the size of the prostate, thereby alleviating the static component of BOO. However, the symptomatic improvement following this therapy is significantly less than that following surgery. The lesser efficacy is likely mechanism-based in that 5a-reductase inhibitors decrease the size of the prostate by reducing the amount of epithelial tissue without affecting the smooth muscle, therefore the dynamic component of BOO may still be present.

Another pharmacological therapy involves the administration of subtype nonselective alpha-1 adrenergic receptor antagonists. These agents relax the prostatic-urethral smooth muscle by blocking endogenous sympathetic tone hence affecting the dynamic component of BOO. However, these agents were originally developed to treat hypertension and have effects on the cardiovascular system which include decreasing blood pressure and causing orthostatic hypotension. The efficacy of this therapy is also significantly less than that following surgery. Efficacy of these agents may be limited by dose-related cardiovascular side-effects, the remaining static component of BOO, and/or because another endogenus substance contributes to the dynamic prostatic-urethral tone.

The predominant alpha-1 adrenergic receptor subtype responsible for alpha 1 agonist mediated contraction of human prostatic-urethral smooth muscle is the alpha-1a subtype. Animal studies suggest that the alpha-1a receptor is not involved in normal blood pressure regulation, therefore selective alpha-1a receptor antagonists may not have the dose-limiting side-effects of subtype nonselective antagonists. The only other substances identified to potently contract human prostate tissue are endothelins (ET) via both the ET-A and ET-B receptors. Endothelin-1 is found in very high concentrations in the prostate and appears to be produced locally in the epithelial tissue in the prostate (Langenstroer, et al 1993 J. of Urology 149:495–99). Alpha adrenergic tone is known to be involved in the dynamic component of BPH based on the efficacy of the subtype nonselective compounds approved for clinical use. The role of ET in BPH is unknown at this time.

It is therefore an object of the invention to find an improved therapy for treating benign prostatic hyperplasia. It is a further object of the invention to find improved methods for relaxing lower urinary tract tissue in patients in need of such treatment. Still a further object of the present invention is to improve lower urinary tract symptoms which include increasing urine flow rate, decreasing residual urine volume and improving overall obstructive and irritative symptoms in patients with benign prostatic hyperplasia or symptomatic prostatism.

It has now been found that combination therapy with an alpha-1a antagonist and an endothelin antagonist, preferably a mixed ET-A/ET-B antagonist, is useful for treating benign prostatic hyperplasia, for relaxing lower urinary tract tissue, and for improving lower urinary tract symptoms which include increasing urine flow rate, decreasing residual urine volume and improving overall obstructive and irritative symptoms in patients with benign prostatic hyperplasia or symptomatic prostatism. The advantage of the combined administration of an alpha-1a antagonist and an ET-A/ET-B antagonist is that two putative components which determine the dynamic prostatic tone would be inhibited without the dose-limiting side-effects observed with subtype non selective alpha-1 antagonists.

SUMMARY OF THE INVENTION

The present invention provides a composition comprising an alpha-1a adrenergic receptor antagonist and an endothelin antagonist, and pharmaceutically acceptable salts thereof.

In one embodiment of the instant invention is the composition of an alpha-1a adrenergic receptor antagonist and an endothelin antagonist wherein the alpha-1a adrenergic receptor antagonist is a selective alpha-1a adrenergic receptor antagonist; and the pharmaceutically acceptable salts thereof.

In a class of the embodiment is the composition comprising a selective alpha-1a adrenergic receptor antagonist and an endothelin antagonist wherein the selective alpha-1a adrenergic receptor antagonist is selected from Compound A, Compound C, Compound D, Compound E, KMD-3213, tamsulosin, REC 15/2739 or A131701; and the pharmaceutically acceptable salts thereof.

In a subclass of the embodiment is the composition mentioned above wherein the selective alpha-1a adrenergic receptor antagonist is Compound A.

In another subclass of the embodiment is the composition mentioned above wherein the selective alpha-1a adrenergic receptor antagonist is Compound C.

In another subclass of the embodiment is the composition mentioned above wherein the selective alpha-1a adrenergic receptor antagonist is Compound D.

In another subclass of the embodiment is the composition mentioned above wherein the selective alpha-1a adrenergic receptor antagonist is Compound E.

In a second class of the embodiment is the composition comprising an alpha-1a adrenergic receptor antagonist and an endothelin antagonist wherein the endothelin antagonist is a subtype non-selective endothelin antagonist; and the pharmaceutically acceptable salts.

In a subclass of the second class of the embodiment is the composition wherein the subtype non-selective endothelin antagonist is selected from Compound B, bosentan, SB217242, SB209670, A 127722 or A 182086.

Illustrating the subclass is the composition wherein the subtype non-selective endothelin antagonist is Compound B.

Illustrating the embodiment is the composition comprising a selective alpha-1a adrenergic receptor antagonist and an endothelin antagonist wherein the selective alpha-1a adrenergic receptor antagonist is Compound A, Compound D, Compound E, or a pharmaceutically acceptable salt thereof; and the endothelin antagonist is Compound B or a pharmaceutically acceptable salt thereof.

Illustrating the embodiment is the composition comprising a selective alpha-1a adrenergic receptor antagonist and an endothelin antagonist wherein the selective alpha-1a adrenergic receptor antagonist is Compound A and the endothelin antagonist is Compound B; and pharmaceutically acceptable salts thereof.

Also illustrating the embodiment is the composition comprising a selective alpha-1a adrenergic receptor antagonist and an endothelin antagonist wherein the selective alpha-1a adrenergic receptor antagonist is Compound D and the endothelin antagonist is Compound B; and pharmaceutically acceptable salts thereof.

Also illustrating the embodiment is the composition comprising a selective alpha-1a adrenergic receptor antagonist and an endothelin antagonist wherein the selective alpha-1a adrenergic receptor antagonist is Compound E and the endothelin antagonist is Compound B; and pharmaceutically acceptable salts thereof.

Further illustrating the embodiment is the composition comprising an alpha-1a adrenergic receptor antagonist, an endothelin antagonist, a 5a-reductase inhibitor, and pharmaceutically acceptable salts thereof.

A second embodiment of the invention is a method of treating benign prostatic hyperplasia in a subject in need thereof which comprises administering to the subject an effective amount of an alpha-1a antagonist, an endothelin antagonist, and optionally a 5a-reductase inhibitor.

A class of the second embodiment is the method wherein the alpha-1a adrenergic receptor antagonist is selected from Compound A, Compound D, Compound E, KMD-3213, tamsulosin, REC 15/2739, A131701, or pharmaceutically acceptable salts thereof; and the endothelin antagonist is selected from Compound B, bosentan, SB217242, SB209670, A 127722, A 182086, or pharmaceutically acceptable salts thereof.

A subclass of the second embodiment is the method wherein the alpha-1a adrenergic receptor antagonist is Compound D or a pharmaceutically acceptable salt thereof, and the endothelin antagonist is Compound B or a pharmaceutically acceptable salt thereof Another subclass of the second embodiment is the method wherein the alpha-1a adrenergic receptor antagonist is Compound E or a pharmaceutically acceptable salt thereof, and the endothelin antagonist is Compound B or a pharmaceutically acceptable salt thereof.

Another class of the second embodiment is the method wherein the alpha-1a adrenergic receptor antagonist is selected from Compound A, Compound C, KMD-3213, tamsulosin, REC 15/2739 or A131701 and the endothelin antagonist is selected from Compound B, bosentan, SB217242, SB209670, A 127722 or A 182086.

A subclass of the second embodiment is the method wherein the alpha-1a adrenergic receptor antagonist is Compound A and the endothelin antagonist is Compound B.

Another subclass of the second embodiment is the method wherein the alpha-1a adrenergic receptor antagonist is Compound C and the endothelin antagonist is Compound B.

A third embodiment of the instant invention is a method of relaxing lower urinary tract tissue in a subject in need thereof which comprises administering to the subject an effective amount of an alpha-1a antagonist, an endothelin antagonist, and optionally a 5a-reductase inhibitor.

A class of the third embodiment is the method wherein the alpha-1a adrenergic receptor antagonist is selected from Compound A, Compound D, Compound E, KMD-3213, tamsulosin, REC 15/2739, A131701, or pharmaceutically acceptable salts thereof; and the endothelin antagonist is selected from Compound B, bosentan, SB217242, SB209670, A 127722, A 182086, or pharmaceutically acceptable salts thereof.

A subclass of the third embodiment is the method wherein the alpha-1a adrenergic receptor antagonist is Compound D or a pharmaceutically acceptable salt thereof, and the endothelin antagonist is Compound B or a pharmaceutically acceptable salt thereof.

Another subclass of the third embodiment is the method wherein the alpha-1a adrenergic receptor antagonist is Compound E or a pharmaceutically acceptable salt thereof, and the endothelin antagonist is Compound B or a pharmaceutically acceptable salt thereof.

Another class of the third embodiment is the method wherein the alpha-1a adrenergic receptor antagonist is selected from Compound A, Compound C, KMD-3213, tamsulosin, REC 15/2739 or A131701 and the endothelin antagonist is selected from Compound B, bosentan, SB217242, SB209670, A 127722 or A 182086.

A subclass of the third embodiment is the method wherein the alpha-1a adrenergic receptor antagonist is Compound A and the endothelin antagonist is Compound B.

In another subclass of the third embodiment is the method wherein the alpha-1a adrenergic receptor antagonist is Compound C and the endothelin antagonist is Compound B.

A fourth embodiment of the invention is a method of improving lower urinary tract symptoms in a benign prostatic hyperplasia patient which comprises administering to the subject an effective amount of an alpha-1a antagonist, an endothelin antagonist, and optionally a 5a-reductase inhibitor.

A class of the fourth embodiment is method for increasing urine flow rate.

A second class of the fourth embodiment is the method for decreasing residual urine volume.

A third class of the fourth embodiment is a method of improving lower urinary tract symptoms in a benign prostatic hyperplasia patient which comprises administering to the subject an effective amount of an alpha-1a antagonist, an endothelin antagonist, and optionally a 5a-reductase inhibitor wherein the alpha-1a adrenergic receptor antagonist is selected from Compound A, Compound C, KMD-3213, tamsulosin, REC 15/2739 or A131701 and the endothelin antagonist is selected from Compound B, bosentan, SB217242, SB209670, A 127722 or A 182086.

A fourth class of the fourth embodiment is a method of improving lower urinary tract symptoms in a benign prostatic hyperplasia patient which comprises administering to the subject an effective amount of an alpha-1a antagonist, an endothelin antagonist, and optionally a 5a-reductase inhibitor wherein the alpha-1a adrenergic receptor antagonist is selected from Compound A, Compound D, Compound E, KMD-3213, tamsulosin, REC 15/2739, A131701, or pharmaceutically acceptable salts thereof; and the endothelin antagonist is selected from Compound B, bosentan, SB217242, SB209670, A 127722, A 182086, or pharmaceutically acceptable salts thereof.

A subclass of the fourth embodiment is the method wherein the alpha-1a adrenergic receptor antagonist is Compound A and the endothelin antagonist is Compound B.

Another subclass of the fourth embodiment is the method wherein the alpha-1a adrenergic receptor antagonist is Compound C and the endothelin antagonist is Compound B.

Still another subclass of the fourth embodiment is the method wherein the alpha-1a adrenergic receptor antagonist is Compound D or a pharmaceutically acceptable salt thereof, and the endothelin antagonist is Compound B or a pharmaceutically acceptable salt thereof.

Still another subclass of the fourth embodiment is the method wherein the alpha-1a adrenergic receptor antagonist is Compound E or a pharmaceutically acceptable salt thereof, and the endothelin antagonist is Compound B or a pharmaceutically acceptable salt thereof.

A fifth embodiment of the invention is a pharmaceutical composition comprising an alpha-1a adrenergic receptor antagonist and an endothelin antagonist, and pharmaceutically acceptable salts thereof, and a pharmaceutically acceptable carrier.

A class of the fifth embodiment is a pharmaceutical composition comprising an alpha-1a adrenergic receptor antagonist and an endothelin antagonist, wherein the alpha-1a adrenergic receptor antagonist is Compound A and the endothelin antagonist is Compound B, and pharmaceutically acceptable salts thereof, and a pharmaceutically acceptable carrier.

Another class of the fifth embodiment is a pharmaceutical composition comprising an alpha-1a adrenergic receptor antagonist and an endothelin antagonist, wherein the alpha-1a adrenergic receptor antagonist is Compound C and the endothelin antagonist is Compound B, and pharmaceutically acceptable salts thereof, and a pharmaceutically acceptable carrier.

Another class of the fifth embodiment is a pharmaceutical composition comprising an alpha-1a adrenergic receptor antagonist and an endothelin antagonist, wherein the alpha-1a adrenergic receptor antagonist is Compound D and the endothelin antagonist is Compound B, and pharmaceutically acceptable salts thereof, and a pharmaceutically acceptable carrier.

Another class of the fifth embodiment is a pharmaceutical composition comprising an alpha-1a adrenergic receptor antagonist and an endothelin antagonist, wherein the alpha-1a adrenergic receptor antagonist is Compound E and the endothelin antagonist is Compound B, and pharmaceutically acceptable salts thereof, and a pharmaceutically acceptable carrier.

Exemplifying the invention is a pharmaceutical composition made by combining an alpha-1a antagonist, an endothelin antagonist, and pharmaceutically acceptable salts thereof, and a pharmaceutically acceptable carrier.

Further exemplifying the invention is a process for making a pharmaceutical composition comprising combining an alpha-1a antagonist, an endothelin antagonist, and pharmaceutically acceptable salts thereof, and a pharmaceutically acceptable carrier.

DETAILED DESCRIPTION OF THE INVENTION

This invention relates to combination therapy for the treatment of benign prostatic hyperplasia comprising an alpha-1a antagonist and an endothelin antagonist. More specifically he use of a selective alpha-1a adrenergic receptor antagonist in combination with a subtype non-selective endothelin antagonist, and optionally a 5a-reductase inhibitor (e.g., finasteride), provides relief of lower urinary tract symptoms in patients with symptomatic prostatism or benign prostatic hyperplasia. This combination therapy improves lower urinary tract symptoms including increasing urine flow rate, decreasing residual urine volume and improving overall obstructive and irritative symptoms in patients with benign prostatic hyperplasia or symptomatic prostatism. The combinations of the present invention result in improvement of symptoms associated with BPH by blocking endogenous noradrenergic and endothelin-mediated smooth muscle contraction of the smooth muscle in the lower urinary tract including the prostate, urethra, bladder neck and detrusor to reduce bladder outlet obstruction, improve bladder compliance, and/or decrease detrusor instability.

For use in medicine, the salts of the compounds of this invention refer to non-toxic "pharmaceutically acceptable salts." Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid.

The instant invention includes the combination wherein all of the individual components are in the form of pharmaceutically acceptable salts and the combination wherein one or more of the individual components is in the form of a pharmaceutically acceptable salt while other of the components are used as the free base.

Recently, a number of alpha-1a adrenergic receptor antagonist compounds have been disclosed as being useful in the treatment of BPH. These alpha-1a adrenergic receptor antagonists and their utility in treating BPH and inhibiting contraction of lower urinary tract tissue are described in PCT International Application Publication No. WO 96/14846, published May 23, 1996. More particularly, the compound (+)-5-Methoxycarbonyl-6-(3,4-difluorophenyl-4-methoxymethyl-1-{N-[3-(4-(2-pyridyl)piperdin-1-yl) propyl]}-carboxamido-2-oxo-1,2,3,6-tetrahydropyrimidine, disclosed in Example 30 of WO 96/14846, and-referred to herein as "Compound A," is a potent and selective antagonist of the alpha-1a adrenergic receptor antagonist and is useful in the treatment of BPH.

Compound A

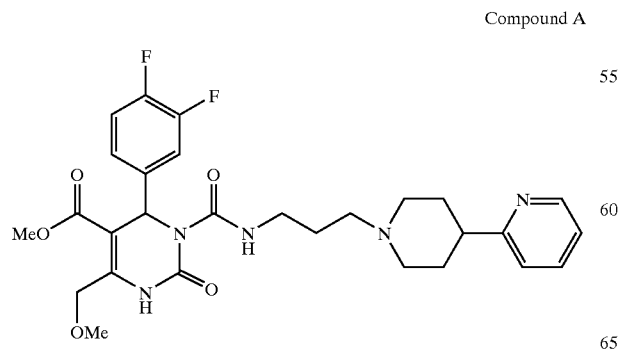

Compound A is prepared according to the procedure of Example 30 in WO 96/14846 or according to the processes disclosed in detail herein. The identification of Compound A as an alpha-1a adrenergic receptor antagonist was established according to the assays described in WO 96/14846.

Compound A, and pharmaceutically acceptable salts thereof exhibit high selectivity for the human alpha-1a adrenergic receptor. One implication of this selectivity is that these compounds display selectivity for lowering intraurethral pressure without substantially affecting diastolic blood pressure.

The term "Compound C" as used herein is trans(+)-4-(3, 4-Difluorophenyl)-5-methyl-2-oxo-oxazolidine-3-carboxylic acid {3-[4-(4-fluorophenyl)-piperidin-1-yl] propyl}amide, a potent and selective antagonist of the alpha-1a adrenergic receptor antagonist useful in the treatment of BPH.

Compound C

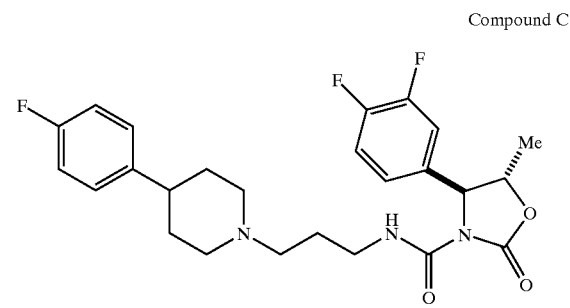

Compound C is prepared according to the procedures described herein.

The term "Compound D" as used herein is (−)-4-(3,4-difluorophenyl)-6-methoxymethyl-2-oxo-1,2,3,4-tetrahydro-pyrimidine-5-carboxylic acid {3-[4-(4-fluorophenyl)-piperidin-1-yl]-propyl}-amide. Compound D is a potent and selective antagonist of the alpha-1a adrenergic receptor antagonist useful in the treatment of BPH.

Compound D

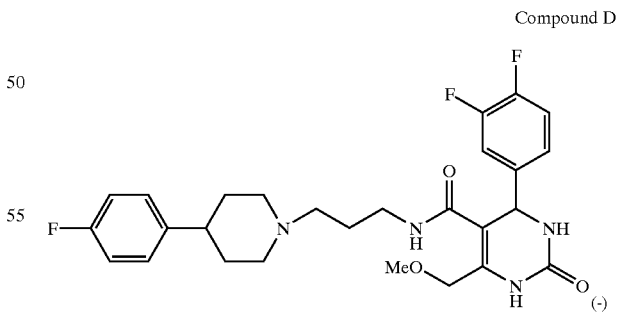

Compound D can be prepared as described below.

The term "Compound E" as used herein is (4S)trans-4-(3,4-difluorophenyl)-3-[1-(4-pyridin-2-yl-cyclohexyl)-(3R)-pyrrolidin-3-ylcarbamoyl]-6-methyl-2-oxo-1,2,3,4-tetrahydro-pyrimidine-5-carboxylic acid methyl ester.

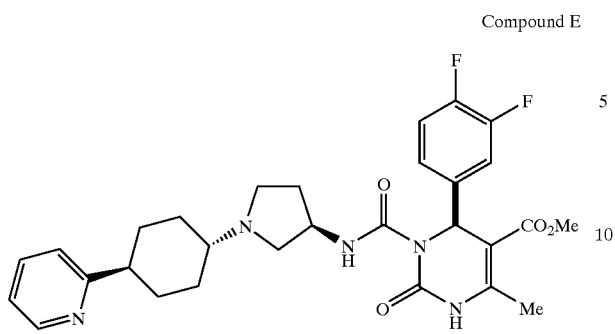

Compound E

Compound E is a potent and selective antagonist of the alpha-1a adrenergic receptor antagonist useful in the treatment of BPH. Compound E is disclosed in WO 98/57641 and can be prepared in accordance with the procedure of Example 48 in WO 98/57641.

KMD-3213 is 1-(3-Hydroxypropyl)-5-[2-[2-[2-(2,2,2-trifluoroethoxy)phenoxy]ethylamino]propyl]indoline-7-carboxamide.

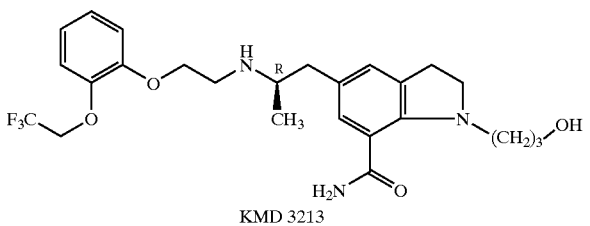

KMD 3213

KMD-3213 is useful in the treatment of dysuria and can be prepared according to the procedures contained in U.S. Pat. No. 5,387,603 which issued, Feb. 7, 1995.

Tamsulosin is (R)-5-[2-[[2-(2-Ethoxyphenoxy) ethyl] amino]propyl]-2-methoxybenzenesulfonamide monohydrochloride, also known as tamsulosin hydrochloride, LY253351, R-(−)-YM-12617, YM-12617-1, YM617, and FLOMAX®.

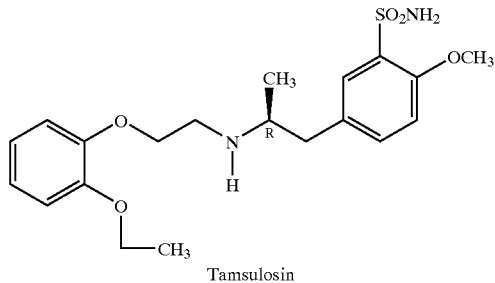

Tamsulosin

Tamsulosin is an alpha 1-a adrenergic receptor antagonist and can be prepared according to the procedures outlined in U.S. Pat. No. 4,703,063.

REC 15/2739 is N-[3-[4-(2-Methoxyphenyl1-piperazinyl]propyl]-3-methyl-4-oxo-2-phenyl-4H-1-benzopyran-8-carboxamide, also known as Recordati 15/2739 or SB 216469.

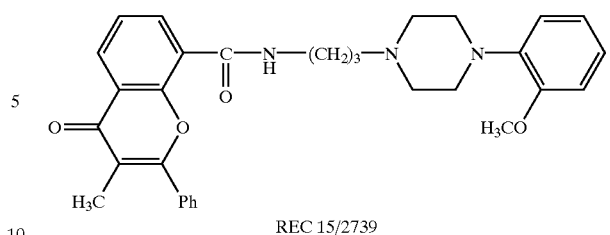

REC 15/2739

REC 15/2739 is an alpha 1-a adrenergic receptor antagonist and can be prepared according to the procedures described in U.S. Pat. No. 5,403,842 which issued on Apr. 4, 1995.

A131701 is (3aR-cis)-3-[2-(1,3,3a,4,5,9b-hexahydro-6-methoxy-2H-benz[e]isoindol-2-yl)ethyl]-pyrido[2',3':4,5]thieno[3,2-d]pyrimidine-2,4(1H,3H)-dione.

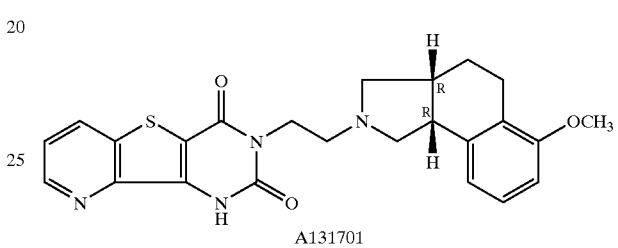

A131701

A131701 is an alpha 1-a adrenergic receptor antagonist and can be prepared according to the procedures outlined in U.S. Pat. No. 5,597,823 which issued on Jan. 28, 1997.

A number of endothelin antagonists have been disclosed as useful for inhibiting vasoconstriction. This antagonism can be helpful in alleviating the symptoms of BPH. These endothelin antagonists and their utility as inhibitors of vasoconstriction are described in U.S. Pat. No. 5,389,629, which issued on Feb. 14, 1995. More particularly, BQ-4508-2 disclosed in U.S. Pat. No. 5,389,620, and referred to herein as "Compound B," is a potent subtype non-selective endothelin antagonist.

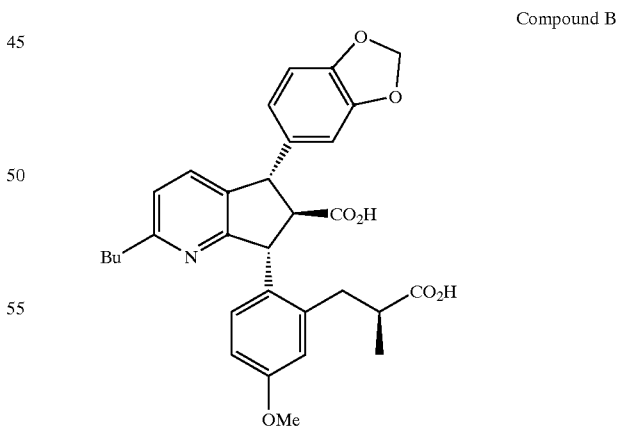

Compound B

Compound B can be prepared according to the procedures described in U.S. Pat. No. 5,389,620 or according to the process disclosed herein.

Compound B and the pharmaceutically acceptable salts thereof inhibit endothelin, which induces sustained contraction of either vascular or non-vascular smooth muscle. By inhibiting endothelin, Compound B can effect a relaxation of smooth muscle tissue and prove helpful in treating BPH.

Bosentan is p-tert-Butyl-N-[6-(2-hydroxyethoxy)-5-(o-methoxyphenoxy)-2-(2-pyrimidinyl)-4-pyrimidinyl]benzenesulfonamide monohydrate, also known as Ro-47-0203/029.

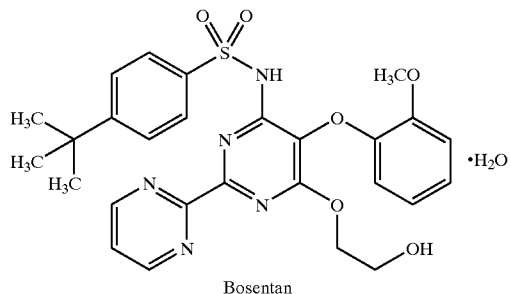

Bosentan

Bosentan is an endothelin antagonist and can be prepared according to the procedures described in U.S. Pat. No. 5,292,740 which issued Mar. 8, 1994.

SB217242 is [1S-(1.alpha.,2.beta.,3.alpha.)]-1-(1,3-benzodioxol-5-yl)-2,3-dihydro-3-[2-(2-hydroxyethoxy)-4-methoxyphenyl]-5-propoxy-1H-Indene-2-carboxylic acid.

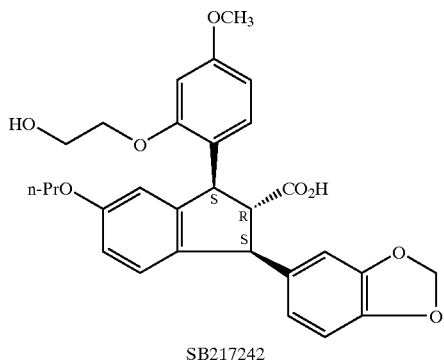

SB217242

SB217242 is an endothelin antagonist and can prepared according to the procedures described in WO 94/25013 which published on Nov. 10, 1994.

SB209670 is [1S-(1.alpha.,2.beta.,3.alpha.)]-1-(1,3-benzodioxol-5-yl)-3-[2-(carbomethoxy)-4-methoxyphenyl]-2,3,-dihydro-5-propoxy-1H-Indene-2-carboxylic acid.

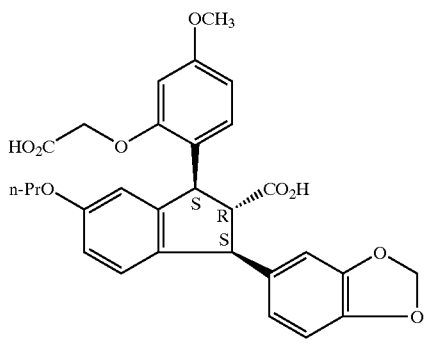

SB209670

SB209670 is an endothelin antagonist and can be prepared according to the procedures described in WO 94/25013 which published on Nov. 10, 1994.

A 127722 is (2.alpha.,3.beta.,4.alpha.)-4-(1,3-Benzodioxol-5-yl)-1-[2-(dibutylamino)-2-oxoethyl]-2-(4-methoxyphenyl)3-pyrrolidinecarboxylic acid.

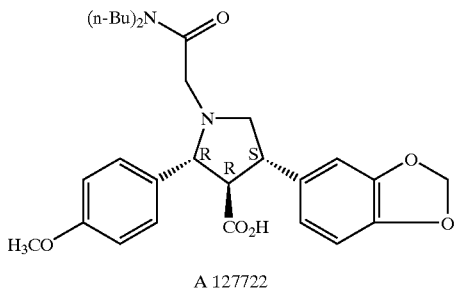

A 127722

A 127722 is an endothelin antagonist and can be prepared according to the procedures outlined in WO 96/06095 which published on Feb. 29, 1996.

A 182086 is [2R-(2.alpha.,3.beta.,4.alpha.)]-4-(1,3-Benzodioxol-5-yl)-2-(3-fluro-4-methoxyphenyl)-1-[2-[(pentylsulfonyl)propylamino]ethyl]-3-pyrrolidinecarboxylic acid.

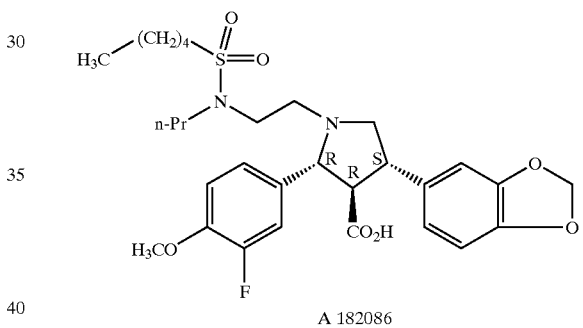

A 182086

A 182086 is an endothelin antagonist and can be prepared according to the procedures outlined in WO 97/30045 which published on Aug. 21, 1997.

For the utility employed herein, the end product compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

These pharmaceutical compositions may be in the form of orally-administrable suspensions or tablets; nasal sprays; sterile injectable preparations, for example, as sterile injectable aqueous or oleaginous suspensions or suppositories.

In accordance with the method of the present invention, the individual components of the combination can be administered separately at different times during the course of therapy or concurrently in divided or single combination forms. For example, in a two-component combination including Compound A and Compound B, treatment with Compound B can commence prior to, subsequent to or concurrent with commencement of treatment with Compound A. The instant invention is therefore to be understood as embracing all such regimes of simultaneous or alternating treatment and the term "administering" is to be interpreted accordingly.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

The alpha-1a antagonists may be employed in the present invention over a dosage range of from about 0.01 mg per subject to about 500 mg per subject. More particularly the effective amount of alpha-1a compound is about 0.1 mg to about 60 mg and in a subclass 1 mg to about 20 mg. One exemplification of this subclass ranges from 5 mg to about 20 mg with specific example of 10, 12.5 and 15 mg.

The endothelin antagonists may be employed in the instant invention over a dosage range of from about 0.1 to 750 mg. More particularly the dosage will vary from about 0.1 to about 100 mg and for the more potent compounds from 0.1 to about 2 mg.

Optionally the composition or method of the instant invention, employs a 5 alpha reductase inhibitor e.g., finasteride. A suitable dosage range for this 5 alpha reductase inhibitor is 1 mg to 10 mg exemplified by 5 mg. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The term "Compound A," as used herein refers to the free base shown below:

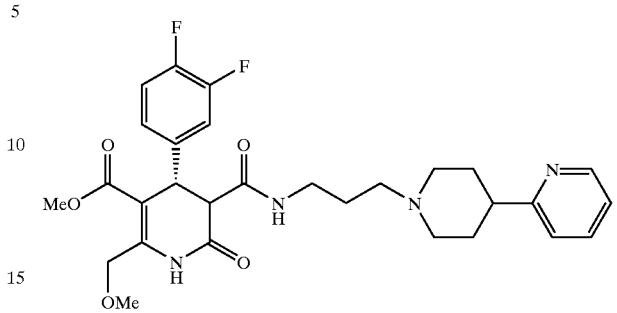

Compound A

Compound A and its utility for antagonizing the alpha-1a adrenergic receptor, for treating BPH and for inhibiting lower urinary tract tissue is described in detail in WO 96/14846. Compound A is readily prepared according to the procedure of Example 30 in WO 96/14846, or according to the processes disclosed herein.

The term "selective alpha-1a adrenergic receptor antagonist," as used herein, refers to an alpha-1a antagonist compound which is at least ten fold selective for the human alpha-1a adrenergic receptor as compared to the human alpha 1b, alpha 1d, alpha 2a, alpha 2b and alpha 2c adrenergic receptors. Methods of identification of selective alpha-1a receptor antagonists are disclosed in U.S. Pat. No. 5,403,847 which issued on Apr. 4, 1995.

The term "lower urinary tract tissue," as used herein, refers to and includes, but is not limited to, prostatic smooth muscle, the prostatic capsule, the urethra and the bladder neck.

The term "improving lower urinary tract symptoms" as used herein includes increasing urine flow rate, decreasing residual urine volume and improving overall obstructive and irritative symptoms in patients with benign prostatic hyperplasia or symptomatic prostatism.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated. Since the instant invention refers to compositions comprising two or more agents, the "therapeutically effective amount" is that amount of the combination of the agents taken together so that the combined effect elicits the desired biological or medicinal response. For example, the therapeutically effective amount of a composition comprising Compound A and Compound B would be the amount of Compound A and the amount of Compound B that when taken together have a combined effect that is therapeutically effective.

As used herein, the term "composition" is intended to encompass a product comprising the specified ingredients in the specified amounts, as well as any product which results, directly or indirectly, from combination of the specified ingredients in the specified amounts.

Abbreviations used in the instant specification, particularly the Schemes and Examples, are as follows:

Aq=aqueous
Ac=acetyl
CDI=carbonyl diimidazole
DMF=N,N-dimethylformamide
DMSO=dimethylsulfoxide
EDC=1-(3-dimethylaminopropyl)-3-ethylcarbodiimide hydrochloride
EtOAc=ethyl acetate
EtOH=ethanol
HOAt=1-hydroxy-7-azabenzotriazole
IPAc=isopropyl acetate
LDA=lithium diisopropylamide
Me=methyl
MeOH=methanol
MTBE=methyl tert-butyl ether
t-Bu=tertiary -butyl or tert-butyl
THF=tetrahydrofuran The end product Compound A L-tartrate salt, i.e., (+)-5-Methoxycarbonyl-6-(3,4-difluorophenyl)-4-methoxycarbonyl-1-{N-[3-(4-(2-pyridyl)piperidin-1-yl)propyl]}-carboxamido-1,2,3,6-tetrahydro-2-oxopyrimidine L-tartrate salt, (1) may be prepared according to Scheme 1. Racemic 2 is readily prepared from commercially available 3,4-difluorobenzaldehyde, methyl 4-methoxyacetoacetate, and urea following the teaching of PCT International Application Publication No. WO 97/21687, published Jun. 19, 1997. Enantiomeric resolution to afford (+)-2 may be accomplished by conventional techniques known to those skilled in the art, or by removing (−)-2 via ester hydrolysis with commercially available protease enzyme, for example, Subtilisin. (+)-2 is coupled with 3-[4-(2-pyridyl)piperidin-1-yl] propylamine, (6) (Scheme 3), utilizing carbonyl diimidazole, to afford (+)-5-methoxycarbonyl-6-(3,4-difluorophenyl)-4-methoxycarbonyl-1-{N-[3-(4-(2-pyridyl)piperidin-1-yl)propyl]} carboxamido-1,2,3,6-tetrahydro-2-oxopyrimidine, (3). Crystallization of the (+)-5-methoxycarbonyl-6-(3,4-difluorophenyl)-4-methoxycarbonyl-1-{N-[3-(4-(2-pyridyl)piperidin-1-yl)propyl]}carboxamido-1,2,3,6-tetrahydro-2-oxopyrimidine L-tartrate salt, (1) is accomplished by treating a solution of 3 with L-tartaric acid.

Scheme 1

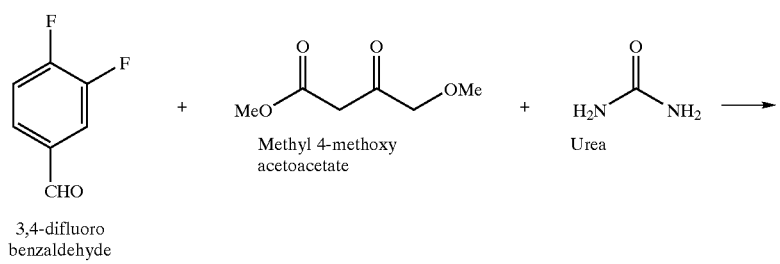

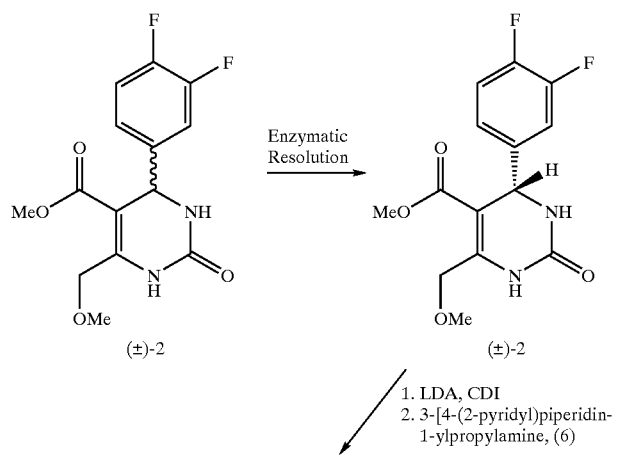

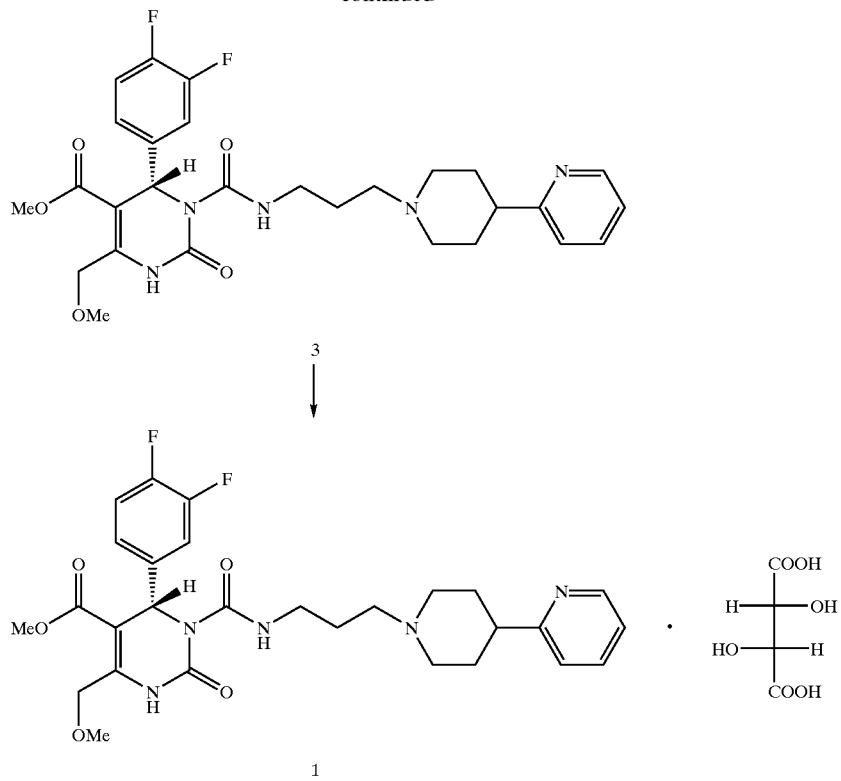

3-[4-(2-pyridyl)piperidin-1-yl]propylamine, (6) can be prepared following the teachings of WO 96/14846, or by the procedure outlined in Scheme 2 wherein commercially available 2,4'-dipyridyl is alkylated with 3-bromopropylamine hydrobromide to afford pyridinium salt 4. Reduction of 4 with sodium borohydride affords 5 which is hydrogenated over Pearlman's catalyst to afford 3-[4-(2-pyridyl)piperidin-1-yl]propylamine, (6). If desired, 6 may be used directly in the preparation of 3, or it may be crystallized as its L-tartrate salt 7.

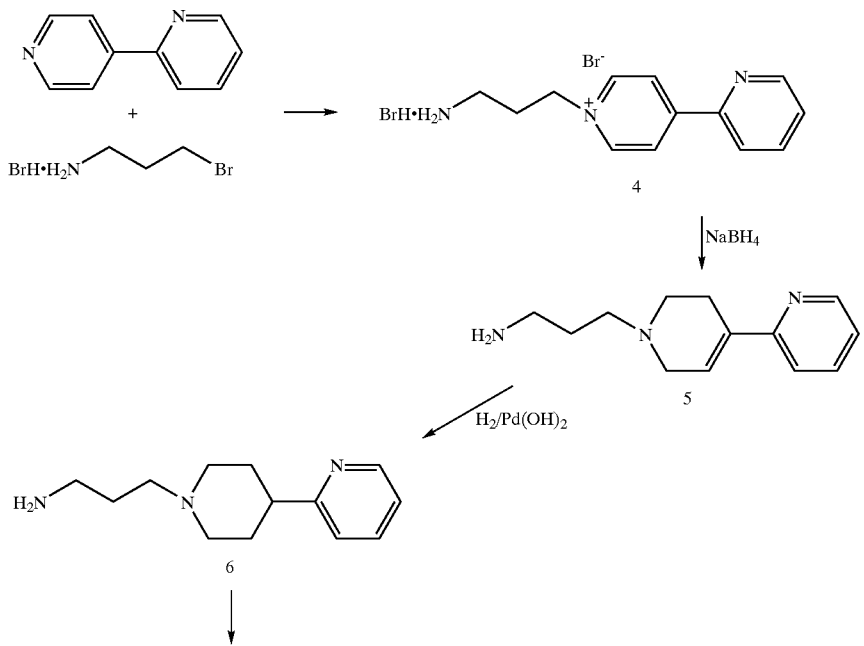

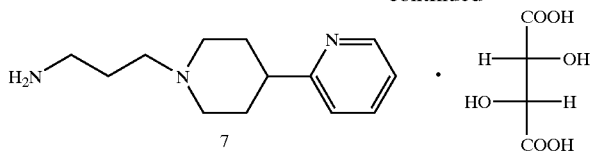
Scheme 3
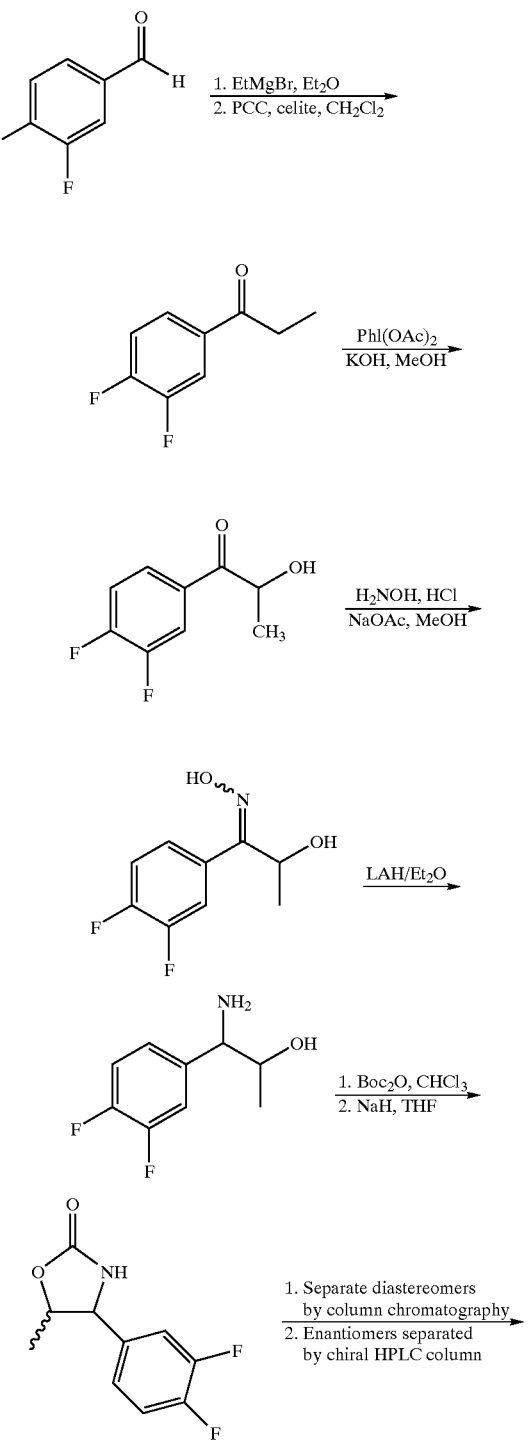
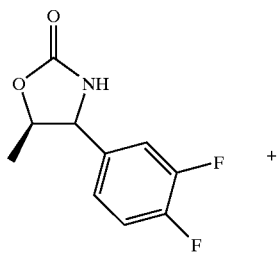
Relative stereochemistry shown for the cis and trans isomers
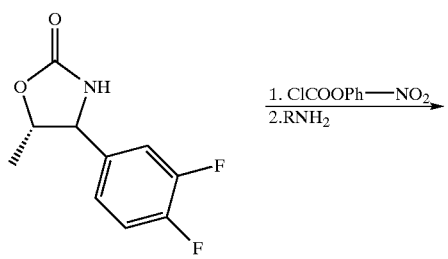
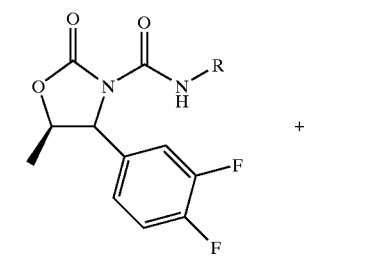
Only two of the possible four structures shown.
Absolute stereochemistry was not established
The following examples are provided to further define the invention without, however, limiting the invention to the particulars of these examples.

EXAMPLE 1

1-(3-Aminopropyl)-4-(2-pyridyl)pyridinium Bromide Hydrobromide, (4)

A solution of 2,4'-dipyridyl (820 g, 5.25 mol) and 3-bromopropylamine hydrobromide (1400 g, 6.39 mol) in DMF (5.0 L) was heated to 95° C. for 8 hours. The reaction mixture was cooled to room temperature and methyl tert-butyl ether (3.7 L) was added over 3 hours. The slurry was stirred for 1 hour and filtered. The solid was washed with MTBE/DMF (1:1, 4.2 L) and dried to afford 1-(3-aminopropyl)-4-(2-pyridyl)pyridinium bromide hydrobromide as a tan solid.

EXAMPLE 2

3-[4-(2-Pyridyl)-3,4-dehydropiperidin-1-yl] propylamine, (5)

A suspension of 1-(3-aminopropyl)-4-(2-pyridyl)-pyridinium bromide hydrobromide, (4), (1840 g, 4.9 mol) in methanol (18 L) was cooled to 5° C. Sodium borohydride (612 g, 16.2 mol) was added in small portions over 2 hours. Methanol was removed by distillation under reduced pressure. Methyltert-butyl ether (10 L) and 20 wt % aqueous NaOH (20 L) were added. The mixture was stirred for 20 min and the two layers were separated. The aqueous layer was extracted with MTBE (10 L). The combined MTBE extract was concentrated under vacuum to afford 5 as a thick oil, which was dissolved in MeOH (8 L) and used in the next step without further treatment.

EXAMPLE 3

3-[4-(2-Pyridyl)piperidin-1-yl]propylamine, (6)

A solution of 3-[4-(2-pyridyl)3,4-dehydropiperidin-1-yl] propylamine, (5), (900 g, 4.1 mol) in methanol (9 L) was hydrogenated over Pearlman's catalyst (90 g) at 40 psi for 2 hours. The slurry was filtered through Celite® 521, rinsed with methanol (3×300 mL), and the solution was concentrated via rotary evaporation to afford 3-[4-(2-pyridyl) piperidin-1-yl]propylamine, (6), as thick yellow oil.

EXAMPLE 4

3-[4-(2-Pyridyl)piperidin-1-yl]propylamine L-tartrate salt, (7)

A solution of 3-[4-(2-pyridyl)piperidin-1-yl]propylamine, (6), (637.9 g, 3.86 mol) in ethanol (8.5 L) was warmed to 65° C. A solution of L-tartaric acid (637.9 g, 4.25 mol) in ethanol (2.23 L) was added in portions. Approximately 15% of the tartaric acid solution was added and then reaction mixture was aged for 1 hour to afford a thin slurry of crystalline material. The remaining tartaric acid solution was added dropwise. Heating was discontinued and the solution was slowly cooled to ambient temperature overnight. The solids were filtered, rinsed with ethanol (2×1 L) and dried under a stream of nitrogen to afford 3-[4-(2-pyridyl)piperidin-1-yl] propylamine L-tartrate salt, (7), as a pale yellow solid.

EXAMPLE 5

3-[4-(2-Pyridyl)piperidin-1-yl]propylamine (6)

3-[4-(2-pyridyl)piperidin-1-yl]propylamine L-tartrate salt, (7), (1120 g, 3.0 mol) was treated with 5M NaOH (5.7 L, 28.6 mol). The suspension was extracted with isopropyl acetate (3×18 L). The combined extracts were concentrated to afford 3-[4-(2-pyridyl)-piperidin-1-yl]propylamine, (6), as a viscous oil.

EXAMPLE 6

(±)-5-Methoxycarbonyl-6-(3,4-difluorophenyl)-4-methoxymethyl-1,2,3,6-tetrahydro-2-oxopyrimidine, (2)

A solution of methyl 4-methoxyacetoacetate (702 g, 4.8 mol), urea (433 g, 7.2 mol), 3, 4-difluorobenzaldehyde (670 g, 4.7 mol), boron trifluoride diethyl etherate(1126 g, 7.9 mol), copper(II) acetate (94 g, 0.52 mol), and acetic acid (36 mL) in THF (7.5 L) was heated to reflux for 8 hours. The reaction mixture was cooled to 20° C. Ethyl acetate (8 L) and 10% citric acid aqueous solution (7.5 kg) was added. The two layers were separated and the aqueous layer was extracted with ethyl acetate (4 L). The combined organic layers were washed with 10% aqueous sodium carbonate (2×5 L) and with 5% brine (1×5 L). The organic layer was concentrated under reduced pressure, with toluene being added continuously and the mixture was concentrated until the level of THF and ethyl acetate was <0.5% volume to toluene, to a final volume was about 2.5 L. The toluene slurry was warmed to 80° C. to dissolve the solids. The solution was cooled slowly to 60° C. and seeded. The slurry was aged at 60° C. for 1 hour and cooled slowly to 20° C. over 4 hours. Hexane (700 mL) was added over 30 minutes. The slurry was aged for 1 hour and filtered. The solid was washed with toluene (1.5 L) and dried to afford (±)-2 as a white solid.

EXAMPLE 7

(+)-(6S)-5-Methoxycarbonyl-6-(3,4-difluorophenyl)-4-methoxymethyl-1,2,3,6-tetrahydro-2-oxopyrimidine, ((+)-2)

A 100-L reaction vessel was charged with 50 mM Tris buffer (Tris HCl (77.4 g) and Tris Base (196.7 g) in deionized water (42.3 L)), subtilisin (12.0 L, Genencor Purafect 4000L), acetonitrile (5.7 L), and (±)-5-methoxycarbonyl-6-(3,4-difluorophenyl)-4-methoxymethyl-1,2,3,6-tetrahydro-2-oxopyrimidine, (2), (120 g, 0.38 mol) and the mixture was allowed to react at 37° C., pH 8.3 for 9 days. The reaction mixture was extracted with toluene (10 L). The aqueous layer was separated and washed with toluene (5 L). The combined organic extracts were washed with brine (10 L). The organic layer was concentrated by rotary evaporation, filtered, then adjusted to 400 mL volume with toluene. The (+)-2 was crystallized by adding heptane (80 mL), followed by seeding. The mixture was stirred for 1 hr, then heptane (520 mL) was added over 8 hrs. The crystals were filtered, washed with 3:2 heptane-toluene (150 mL), then dried under high vacuum to yield (+)-(6S)-5-methoxycarbonyl-6-(3,4-difluorophenyl)-4-methoxymethyl-1,2,3,6-tetrahydro-2-oxopyrimidine, ((+)-2) as a white solid.

EXAMPLE 8

(+)-5-Methoxycarbonyl-6-(3,4-difluorophenyl)-4-methoxycarbonyl-1-{N-[3-(4-(2-pyridyl)piperidin-1-yl)propyl]}carboxamido-1,2,3,6-tetrahydro-2-oxopyrimidine, (3)

A solution of (+(6S)-5-methoxycarbonyl-6-(3,4-difluorophenyl)-4-methoxymethyl-1,2,3,6-tetrahydro-2- oxopyrimidine, ((+)2), (100 g, 0.32 mol) in THF (1L) was cooled to −65° C. A solution of LDA (2M in heptane/THF/ ethylbenzene, 184 mL, 0.36 mol) was added in a thin stream. The resulting clear solution was aged for 15 min., then carbonyl diimidazole (62.3 g, 0.38 mol) was added as a solid in one portion. The resulting slurry was aged for 15 min at ca. −60° C., then warmed to 20° C. and aged for 1 hour. The thin yellow suspension was cooled to −60° C. A solution of 3-[4-(2-pyridyl)piperidin-1-yl]propylamine, (6), (100 g, 0.45 mol) in IPAc was added. The reaction mixture was slowly warmed to 20° C. After 1 hour at 20° C, the reaction was quenched with $H_2O$ (1.5 L) and IPAc (1.5 L). The layers were separated. The organic layer was washed with $H_2O$ (2×1.5 L). The combined aqueous layers were washed with IPAc (1×0.5 L). The combined organic layers were extracted with 2N HCl (1×1 L and 1×0.5 L). The combined HCl extracts were neutralized by the cautious addition of solid NaHCO3 (450 g). IPAc (1 L) and $H_2O$ (1 L) were added to the bicarbonate layer. The layers were separated. The aqueous bicarbonate layer was washed with IPAc (1×1 L). The combined product containing IPAc layers were washed with $H_2O$ (2×1 L). The organic layer was concentrated to afford (+)-5-methoxycarbonyl-6-(3,4-difluorophenyl)-4-methoxycarbonyl-1-{N-[3-(4-(2-pyridyl)piperidin-1-yl)propyl]}carboxamido-1,2,3,6-tetrahydro-2-oxopyrimidine, (3), as a thick oil.

EXAMPLE 9

Crystallization of (+)-5-Methoxycarbonyl-6-(3,4-difluorophenyl)-4-methoxycarbonyl-1-{N-[3-(4-(2-pyridyl)piperidin-1-yl)propyl]}carboxamido-1,2,3,6-tetrahydro-2-oxopyrimidine L-tartrate salt, (1)

Crude (+)-5-methoxycarbonyl-6-(3,4-difluorophenyl)-4-methoxycarbonyl-1-{N-[3-(4-(2-pyridyl)piperidin-1-yl)propyl]}carboxamido-1,2,3,6-tetrahydro-2-oxopyrimidine, (3), (150 g) was dissolved in 2-propanol (1.27 L) at 50° C. Approximately 50 mL of a solution of L-tartaric acid (40.7g) in EtOH (175 mL) was added to the solution of 3 at 50° C. The solution was aged for 1 hour for crystals to develop, then the remaining L-tartaric acid was added over 0.5 hour. The suspension of 1 was cooled to 20° C. After overnight age, the suspension was cooled to 0° C. and filtered. The cake was rinsed with 2-propanol (2×150 mL) and dried by pulling $N_2$ through the cake to afford (+)-5-methoxycarbonyl-6-(3,4-difluorophenyl)-4-methoxycarbonyl-1-{N-[3-(4-(2-pyridyl)piperidin-1-yl)propyl]}carboxamido-1,2,3,6-tetrahydro-2-oxopyrimidine L tartrate salt, (1), as a white, free-flowing solid. This crystalline form of (1), designated as Type A, was determined to be an isopropanol solvate.

$^1$H NMR (DMSO-d$_6$): 9.95 (s, 1H), 8.81 (t, J=5.6, 1H), 8.49 (m, 1H), 7.71 (td, J=7.8, 1.8, 1H), 7.41 (dt, J=10.5, 8.6, 1H), 7.28 (d, J=7.8, 1H), 7.20 (m, 2H), 7.08 (m, 1H), 6.56 (s, 1H), 4.63 (d, J=13.1, 1H), 4.43 (d, J=13.1, 1H), 4.08 (s, 2H), 3.67 (s, 3H), 3.29 (s, 3H), 3.25 (m, 4H), 2.79 (m, 1H), 2.71 (t, J=7.3, 2H), 2.52 (m, 2H), 1.89 (m, 4H), 1.78 (m, 2H). $^{13}$C NMR (DMSO-d$_6$): 173.8, 164.4, 163.4, 152.9, 152.2, 149.2 (dd, J=246.5, 24.7), 149.0 (dd, J=246.5, 24.2), 148.9, 146.8, 138.0 (t, J=4.5), 136.7, 123.0 (dd, J=6.7, 3.5), 121.7, 121.3, 117.9 (d, J=17.2), 115.3 (d, J=17.6), 103.1, 71.8, 66.7, 58.2, 54.4, 52.3, 51.8, 51.7, 41.9, 38.1, 29.7, 24.9.

Type A is characterized by a differential scanning calorimetry (DSC) curve, at a heating rate of 10° C/min in an open cup under flowing nitrogen, exhibiting a relatively broad endotherm with an extrapolated onset temperature of about 56° C., a peak temperature of about 90° C. and an associated heat of about 23 J/gm followed by an endotherm with an extrapolated onset temperature of about 108° C., a peak temperature of about 115° C. and an associated heat of about 13 J/gm followed by an endotherm with an extrapolated onset temperature of about 145° C., a peak temperature of about 148° C. and an associated heat of about 57 J/gm. The two low temperature endotherms are due to the loss of isopropanol and the high temperature endotherm is due to melting with decomposition of the remaining unsolvated phase (Type B).

The X-ray powder diffraction pattern of Type A is characterized by d-spacings of 14.91, 8.32, 6.88, 5.41, 4.74, 4.29, 4.04, 3.86, 3.75 and 3.59 Å.

A second crystalline form of (1), designated as Type B which is unsolvated material, was prepared either by swishing Type A in ethanol followed by filtration and subsequent drying, or by heating Type A to −115° C. for about 20 minutes.

More specifically, Compound A tartrate salt Type A (2-propanol solvate) (10 g) was suspended in ethanol (50 mL) at 0° C. in a flask fitted with a mechanical stirrer, addition funnel, and thermocouple under a $N_2$ atmosphere. The solution was aged for 2 hours and then filtered. The cake was rinsed with ethanol (2×5 mL) and dried by pulling $N_2$ through the cake to afford Compound A tartrate salt Type B as a white, free-flowing solid. The $^1$H and $^{13}$C NMR spectra for Type B are identical to the spectra for Type A shown above.

Type B is characterized by a differential scanning calorimetry (DSC) curve, at a heating rate of 10° C./min in an open cup under flowing nitrogen, exhibiting an endotherm with an extrapolated onset temperature of about 144° C., a peak temperature of about 148° C. and an associated heat of about 65 J/gm. The endotherm is due to melting with decomposition.

The X-ray powder diffraction pattern of Type B is characterized by d-spacings of 13.29, 7.82, 6.63, 6.20, 5.36, 5.01, 4.59, 4.35, 4.05, 3.73 and 3.60 Å.

EXAMPLE 10

Preparation of trans (+)-4-(3,4-Difluorophenyl)-5-methyl-2-oxo-oxazolidine-3-carboxylic acid{3-[4-(4-fluorophenyl)-piperidin-1-yl]propyl}amide a. 1-(3,4-Difluorophenyl)propan-1-ol To a solution of 3,4-difluorobenzaldehyde (5.0 g, 35.2 mmol) in diethyl ether (35 mL) in a round bottom flask was added a solution of ethylmagnesium bromide in THF (38.0 mL, 38.0 mmol) at 0° C. The reaction mixture was stirred at 0° C. for 1 h when TLC analysis indicated that the reaction was complete ($R_f$=0.5, 8:1 hexane/EtOAc). The reaction was quenched carefully by adding 38 mL of water. It was extracted with diethyl ether (2×30 mL), washed with brine and the organic layer was dried over NaSO$_4$. The solvent was removed in vacuo after filtration and 1-(3,4-difluorophenyl)propan-1-ol was obtained as a yellow oil (crude wt.=6.0 g) which looked >90% pure by NMR. It was used in the next step without purification.

b. 1-(3,4-Difluorophenyl)propan-1-one

In a round bottom flask containing pyridinium chlorochromate (12.5 g, 58.1 mmol) was added celite 545 (25 g) and with the help of a magnetic stirrer the solids were mixed together. 200 mL of $CH_2Cl_2$ was added followed by a solution of 1-(3,4-difluorophenyl)propan-1-ol (5.0 g, 29.1 mmol) in 10 mL of $CH_2Cl_2$ and the resulting brown suspension was stirred overnight at room temperature. The suspension was filtered through a sintered glass funnel and the solvent was removed in vacuo from the pale green colored filtrate. The green oil was then diluted with diethyl ether (200 mL) and it was filtered through a pad of celite to remove the metal impurities. The solvent was removed in vacuo to obtain 1-(3,4-difluorophenyl)propan-1-one as a pale yellow oil (3.4 g, 69% yield). It was used ion the next step without purification.

c. 1-(3,4-Difluorophenyl)-2-hydroxy-propan-1-one

In a round bottom flask containing 200 mL of MeOH was added pellets of potassium hydroxide (23.0 g, 410.0 mmol). The solution was cooled to 0° C. and 1-(3,4-difluorophenyl)-2-hydroxy-propan-1-one (7.0 g, 41.2 mmol) in 10 mL MeOH was added dropwise. The solution was stirred for 10 min and then iodobenzene diacetate (22.5 g, 70 mmol) was added in two portions. The solution first became orange and then turned yellow. It was stirred overnight at room temperature and then the solvent was removed in vacuo. The residue was dissolved in water and was extracted with ethyl acetate (3×100 mL). The combined organic extracts were washed with brine and then dried over $NaSO_4$. After filtration, the solvent was removed in vacuo to get 1-(3,4-difluorophenyl)-2-hydroxy-propan-1-one dimethyl acetyl as a yellow viscous oil (crude wt.=9.2 g). It was dissolved in 150 mL of acetone and 10 drops of concentrated sulfuric acid were added. After stirring for 3 h, TLC analysis indicated that the reaction was complete. Acetone was removed in vacuo and after basification with saturated $NaHCO_3$, the residue was extracted in EtOAc and was washed with brine. The organic layer was separated, dried over $Na_2SO_4$ and then filtered. The solvent was removed in vacuo and the residue was purified by silica gel chromatography (Rf=0.4, 3:2 hexane/EtOAc) to obtain 1-(3,4-difluorophenyl)-2-hydroxy-propan-1-one as a pale yellow oil (3.3 g, 51% yield over two steps).

d. 1-(3,4-Difluorophenyl)-2-hydroxy-propan-1-one-oxime

To a well stirred solution of 1-(3,4-difluorophenyl)-2-hydroxy-propan-1-one (5.5 g, 29.6 mmol) in MeOH (200 mL) was added hydroxylamine hydrochloride (2.6 g, 38.4 mmol) and sodium acetate (8.1 g, 59.2 mmol) and the turbid solution was stirred overnight at room temperature. The solvent was evaporated and the residue was extracted with $CH_2Cl_2$. The organic layer was washed with sat. $NaHCO_3$, separated, dried over $NaSO_4$ and then filtered. The solvent was removed in vacuo to obtain 1-(3,4-Difluorophenyl)-2-hydroxy-propan-1-one-oxime as an orangish yellow oil (5.3 g, 97%). It was used in the next step without purification.

e. 1-Amino-1-(3,4-difluorophenyl)-propan-2-ol

To a well stirred solution of 1-(3,4-difluorophenyl)-2-hydroxy-propan-1-one-oxime (5.8 g, 28.4 mmol), was added a 1.0 M solution of $LiAlH_4$ in ether (90 mL, 90 mmol) dropwise at 0° C. The resulting yellow solution was then stirred at room temperature for 2 h. The reaction mixture was cooled to 0° C. and then carefully quenched sequentially with 3.5 mL of water, 3.5 mL of 3N NaOH followed by 10.5 mL of water. The resulting suspension was filtered thru a fritted glass funnel. To the residue was added 100 mL $Et_2O$ and the suspension was heated to reflux for 20 min. The suspension was filtered and was combined with the previous filtrate, dried over $MgSO_4$, filtered and the solvent was removed in vacuo. 1-Amino-1-(3,4-difluorophenyl)-propan-2-ol was obtained as a yellow glassy syrup (3.6 g, 66%) which was used in the next step without further purification.

f. [1-(3,4-Difluorophenyl)-2-hydroxy-propyl]-carbamic acid-tert-butyl ester

To a solution of 1-amino-1-(3,4-difluorophenyl)-propan-2-ol (3.5 g, 19.1 mmol) in $CHCl_3$ (15 mL) at 0° C. was added a solution of di-tert-butyl dicarbonate (5.1 g, 23.6 mmol) in $CHCl_3$ (10 mL) in one portion and the resulting solution was stirred overnight at room temperature. The solvent was removed in vacuo and the residue was subjected to column chromatography on silica gel (2:1 hexane-EtOAc followed by EtOAc) to obtain [1-(3,4-difluorophenyl)-2-hydroxy-propyl]-carbamic acid-tert-butyl ester as a viscous oil (3.3 g, 60.2%).

g. 4-(3,4-Difluorophenyl)-5-methyl-oxazolidin-2-one

To a well stirred solution of [1-(3,4-difluorophenyl)-2hydroxy-propyl]-carbamic acid-tert-butyl ester (0.43 g, 1.5 mmol) THF (20 mL) was added 95% NaH (0.09 g, 3.8 mmol) at room temperature. The resulting suspension was stirred for 3 h at about 35° C. (warm water bath) and then quenched carefully with ice. The biphasic mixture was extracted with 100 mL of EtOAc, washed with brine, dried over $NaSO_4$, filtered and the solvent was removed in vacuo. The two diastereomers were separated by column chromatography over silica gel (First isomer: 0.11 g, $R_f$=0.6, 3:1 hexane-EtOAc; second isomer: 0.23 g, $R_f$=0.5, 3:1 hexane-EtOAc). NOE experiment suggested that the first diastereomer had the methyl and the aryl group in trans configuration while the second diastereomer had cis relationship between the two groups.

Enantiomers of wach of these diastereomers were separated by HPLC using Chiralcel OD (4.6×250 mm) using 80% hexane/20% isopropyl alcohol/0.1% diethylamine as the eluting system (12 mL/min) under isothermal conditions (U.V. 254 nM). The retention times for the two isomers of the trans-oxazolidinone were 12.1 min {$[a]_D$=+36.4 (c=0.25, acetone)} and 15.6 min {$[a]_D$=−30.8 (c=0.20, acetone)}, respectively. The retention times for the two isomers of the cis-oxazolidinone were 13.7 min {$[a]_D$=+65.8 (c=0.92, acetone)} and 19.9 min {$[a]_D$=−65.8 (c=0.74, acetone)}, respectively.

h. 4-(3,4-Difluorophenyl)-5-methyl-2-oxo-oxazolidine-3-carboxylic acid-4-nitro-phenyl ester To a suspension of 95% NaH (0.01 g, .038 mmol) in 5.0 mL of anhydrous THF under argon, a solution of 4-(3,4-difluorophenyl)-5-methyl-oxazolidin-2-one (0.07 g, 0.33 mmol) in 5.0 mL THF was added dropwise via a syringe. The resulting suspension was stirred at room temperature for 20 min. This suspension was then added dropwise via a syringe into another round bottom flask containing a solution of 4-nitrophenylchloroformate (0.08 g, 0.4 mmol) in 10 mL of THF, cooled at −78° C., over a period of 15 min. The stirring was continued for 1 h after which the solvent was removed and the residue was purified be column chromatography on silica gel with 1:1 hexane/CH$_2$Cl$_2$ followed by CH$_2$Cl$_2$ (R$_f$=0.4, CH$_2$Cl$_2$) to obtain 4-(3,4-difluorophenyl)-5-methyl-2-oxo-oxazolidine-3carboxylic acid-4-nitrophenyl ester as a white solid (0.07 g, 56%).

i. 3-[4-(4-Fluoro-phenyl)-piperidin-1-yl]-propylamine

To a solution of 4-fluorophenylmagnesium bromide (110.0 mmol, 55.0 mL of 2.0 M solution) in 150.0 mL THF at 0° C. was added 1-benzyl-4-piperidone (55.0 mmol, 10.2 mL) dropwise. The resulting solution was stirred under argon atmosphere for 1.5 h and then quenched with 100.0 mL of saturated NH$_4$Cl solution. The organic layer was separated and the aqueous layer was extracted with 100.0 mL of Et$_2$O. The combined organic extracts were washed with brine, separated and dried over Na$_2$SO$_4$. The solution was filtered and the solvent was removed in vacuo to obtain a yellow oil which was purified by passing through a silica gel column with 4:1 hexane/EtOAc followed by 1:1 hexane/EtOAc as the eluting system. 1-Benzyl-4-(4-fluoro-phenyl)-piperdin-4-ol was obtained as a pale yellow oil in 89% yield (13.9 g). It was dissolved in 150.0 mL of toluene and p-toluenesulfonic acid monohydrate (50.0 mmol, 9.5 g) was added. The organic extracts were combined, washed with brine and the organic layer was dried over Na$_2$SO$_4$. The solvent was removed in vacuo to obtain 1-benzyl-4-(fluoro-phenyl)-1,2,3,6-tetrahydropyridine as a yellow viscous oil (12.0 g, 92% yield) which was used in the next step without further purification.

To a solution of 1-benzyl-4-(fluoro-phenyl)-1,2,3,6-tetrahydro-pyridine (45.0 mmol, 12.0 g) in 100 mL Me OH was added 1.0 g of Pd(OH)$_2$ and the resulting suspension was hydrogenated under 200 psi of H$_2$ in a stainless steel bomb for two days. The suspension was passed through a pad of celite and the filtrate was concentrated in vacuo to obtain 4-(4-fluoro)-phenyl-piperidine (6.5 g, 94%) as a viscous oil. It was converted into 3-[4-(4-fluoro-phenyl)-piperidin-1-yl)-propylamine.

j. trans (+)-4-(3,4-Difluorophenyl)-5-methyl-2-oxo-oxazolidine-3-carboxylic acid{3-[4-(4-fluorophenyl)-piperidin-1-yl]propyl}amide To a solution of 3-amino-propyl-4-(4-fluoro)phenyl-piperidine (0.04 g, 0.12 mmol) in 10 mL of THF trans (+)-4-(3,4-difluorophenyl)-5-methyl-2-oxo-oxazolidine-3-carboxylic acid-4-nito-phenyl ester (0.03 g, 0.08 mmol) (made from the (+)-enantiomer from HPLC of the trans diastereomer separated by column chromatography) was added and the resulting yellow solution was stirred under argon atmosphere for 10 h at room temperature. The solvent was removed in vacuo and the residue was purified by column chromatography over silica gel with EtOAc followed by 15% MeOH in EtOAcas the eluting systems to obtain trans (+)-4-(3,4-difluorophenyl)-5-methyl-2-oxo-oxazolidine-3-carboxylic acid{3-[4-(4-fluorophenyl)-piperidin-1-yl]propyl}amide in 70% yield. It was converted into its hydrochloride salt.

M.P.=80–83° C. (shrinks around 58° C.); [a]$_D$=+27.4 (c=0.49, MeOH); Anal. Calcd. for C$_{25}$H$_{29}$N$_3$O$_3$F$_3$Cl.1.0 H$_2$O: C, 56.55; H 6.07; N 7.91 Found C, 56.49; H, 5.88; N, 7.80.

EXAMPLE 11

3-[4-(4-Fluorophenyl)piperidin-1-yl]propylamine

Step A. 4-(4-Fluorophenyl)piperidine Hydrochloride

To a solution of 4-(4-fluorophenyl)-1,2,3,6-tetrahydropyridine hydrochloride (10 g) in methanol (200 mL) was added 10% palladium on charcoal (0.5 g) and the mixture was hydrogenated at 50 psi for 3 h. The catalyst was removed by filtration and solvent was evaporated to leave the product as a white powder, which was used in the next step without any purification. The $^1$H-NMR and TLC analysis showed this product to be pure. M.P. 181–182° C.

$^1$H NMR (CDCl$_3$): d 1.95–2.03 (br d, 2H), 2.14–2.29 (m, 2H), 2.70–2.80 (m, 1H), 2.91–3.07 (br q, 2H), 3.60–3.64 (br d, 2H), 6.96–7.03 (m, 2H), 7.19–7.22 (m, 2H), 9.60 (br s, 1H), 9.71 (br s, 1H).

Step B. 3-[4-(4-Fluorophenyl)piperidin-1-yl] Propylphthalimide

A mixture of 4-(4-fluorophenyl)piperidine hydrochloride (5.08 g, 23.2 mmol), 3-bromopropylphthalimide (6.22 g, 23.2 mmol), and potassium carbonate (15 g) in DMF (100 mL) was stirred and heated at 95–100° C. for 12 h. About 80% of the solvent was evaporated at reduced pressure, the residue was diluted with ethyl acetate (200 mL) and washed with brine (3×100 mL) and dried (Na$_2$SO$_4$). Solvent was evaporated and the residue was purified by column chromatography on silica gel using 1/1 hexane-ethyl acetate to 100% ethyl acetate as eluent. This product was crystallized from isopropanol to give a white crystalline solid; m.p. 80–81° C. This material was used in the next step. Concentration of the mother liquor and cooling gave the second crop.

$^1$H NMR (CDCl$_3$): d 1.43–1.52 (m, 2H), 1.67–1.75 (m, 2H), 1.80–1.96 (m, 4H), 2.33–2.46 (m, 3H), 2.94–2.99 (br d, 2H), 3.78 (t, J=7 Hz, 2H), 6.90–7.04 (m, 4H), 7.70–7.74 (m, 2H), 7.84–7.87 (m, 2H).

Step C. 3-[4-(4-Fluorophenyl)piperidin-1-yl]propylamine

To a solution of 3-[4-(4-fluorophenyl)piperidin-1-yl] propylphthalimide (4.5 g, 12.3 mmol) in methanol (200 mL), hydrazine (4 mL) was added and the mixture was stirred and refluxed for 8 h. It was cooled, and the white solid was filtered and washed with methanol (20 mL). Solvent was evaporated, and the residue was dried under vacuum for 4 h. Chloroform (50 mL) was added to this material, it was stirred for 1 h and filtered. The white solid was washed with more chloroform (20 mL), and the solvent was evaporated from the combined filtrates to leave the crude product as an oil. It was purified by column chromatography on silica gel using dichloromethane/methanol/2M ammonia in methanol (10/3/1) as the eluent.

$^1$H NMR (CDCl$_3$): d 1.60–1.83 (m, 6H), 1.96–2.07 (m, 4H), 2.40–2.55 (m, 3H), 2.70–2.85 (br t, 2H), 3.03–3.07 (br d, 2H), 6.93–7.00 (m, 2H), 7.14–7.20 (m, 2H).

EXAMPLE 12

(−)-4-Methoxymethyl-1,2,3,6-tetrahydro-2-oxo-6-(3,4-difluorophenyl)-pyrimidine-5-carboxylic acid

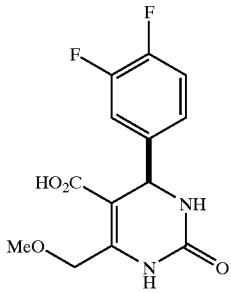

To a well stirred mixture of methyl-4-methoxyacetoacetate (50 g, 0.351 mol), 3,4-difluorobenzaldehyde (51.39 g, 0.351 mmol), and urea (31.64 g, 0.527 mole) in THF (300 mL) at room temperature were added sequentially copper(I) oxide (5.06 g, 0.035 mole) and acetic acid (2.05 mL) followed by the dropwise addition of boron trifluoride diethyl etherate (56 mL, 0.456 mole). The mixture was stirred and refluxed for 8 h, whereupon TLC indicated completion of the reaction. It was cooled and poured into a mixture of ice and sodium bicarbonate (100 g). The resulting mixture was filtered through celite. The celite was washed with dichloromethane (400 mL). The organic layer was separated and the aqueous layer was extracted with dichloromethane (3×300 mL). The combined organic extracts were dried (sodium sulfate) and the solvent was evaporated. The crude product was purified by flash column chromatography on silica gel using 50% ethyl acetate in hexanes and then ethyl acetate as eluent to give the product as a pale yellow foam.

$^1$H NMR (CDCl$_3$) d 3.476 (s, 3H), 3.651 (s, 3H), 4.653 (s, 2H), 5.39 (s, 1H), 6.60 (br s, 1H, NH), 7.00–7.20 (m, 3H), 7.72 (br s, 1H, NH).

The racemic intermediate 5-methoxycarbonyl-4-methoxymethyl-1,2,3,6-tetrahydro-2-oxo-6-(3,4-difluorophenyl)-pyrimidine was resolved by chiral HPLC [Chiralcel OD 20×250 mm #369-703-30604; 1 254 nm; hexanes/ethanol 90/10 ; 85 mg per injection; the 2nd enantiomer peak to elute) to give (−)-5-methoxycarbonyl-4-methoxymethyl-1,2,3,6-tetrahydro-2-oxo-6-(3,4-difluorophenyl)-pyrimidine.

The material is hydrolyzed to the acid by standard means using sodium or lithium hydroxide in methanol.

EXAMPLE 13

(−)-4-(3,4-Difluorophenyl)-6-methoxymethyl-2-oxo-1,2,3,4-tetrahydro-pyrimidine-5-carboxylic acid {3-[4-(4-fluorophenyl)-piperidin-1-yl]-propyl}-amide

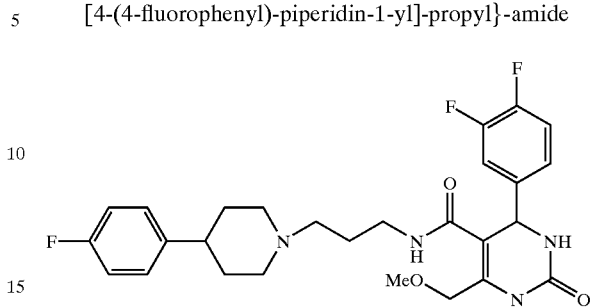

To a suspension of 2.5 g (8.3 mmol) DHP acid prepared in accordance with the procedure of Example 12 and 2.0 g (8.5 mmol) amine prepared in accordance with the procedure of Example 11 in 20 ml DMF was added 1.18 (8.7 mmol) HOAt and 1.65 g (8.6 mmol) EDC. The suspension was stirred 2 h at room temperature, then poured into 700 ml EtOAc and washed with 250 ml saturated aqueous sodium bicarbonate, 300 ml dilute brine, and brine. The organic layer was dried over Na$_2$SO$_4$, filtered, and concentrated. Purification by flash chromatography (7.5×16 cm silica gel, linear gradient 5–10% MeOH/1%NH$_4$OH/CH$_2$Cl$_2$) followed by crystallization from 150 ml of 2:1 EtOAc/hexanes gave the pure title compound. mp 149–150° C.

$^1$H NMR (400 MHz, CDCl$_3$) d 7.38 (s, 1H); 7.20–7.04 (m, 5H); 6.99 (t, 2H, J=8.69 Hz); 6.86 (br t, 1H, J=4.84 Hz); 5.82 (s, 1H); 5.41 (d, 1H, J=2.47 Hz); 4.49 (d, 1H, J=14 Hz); 4.31 (d, 1H, J=14 Hz); 3.42 (s, 3H); 3.37 (m, 1H); 3.21 (m, 1H); 2.93 (d, 1H, J=11.3 Hz); 2.82 (d, 1H, J=11.8 Hz); 2.46 (tt, 1H, J=12.2 and 3.75 Hz); 2.31 (m, 2H); 1.95 (m, 2H); 1.79 (m, 2H); 1.66–1.47 (M, 4H). HRMS (M+H calc 517.2421 found 517.2402). [a]$_D^{23}$−76° (c=0.84 CH$_2$Cl$_2$). Analysis: Calcd. for C$_{27}$H$_{31}$F$_3$N$_4$O$_3$.0.25 H$_2$O; C, 62.23; H, 6.09; N, 10.75; Found: C, 62.17, H, 6.07; N, 10.89.

EXAMPLE 14

Methodology for determining the efficacy of ET antagonists and Alpha-1a antagonists for inhibition of ET-1 and alpha 1 receptor mediated prostatic urethral contractions in a mongrel dog model Methods:

Male mongrel dogs are fasted overnight the anesthetized with Sodium Pentobarbital at 35 mg/kg, iv to effect, followed by a 4 mg/kg/hr iv infusion. A cuffed endotracheal tube is inserted and each animal ventilated with room air using a positive displacement large animal ventilator at a rate of 18 breaths/minute and an average tidal volume of 18 ml/kg body weight. Body temperature is maintained with a heating pad and a temperature controller connected to an esophogeal temperature probe. Two catheters are placed in the aorta via the femoral arteries (one in each artery) for administration of endothelin or phenyephrine and for continuous direct monitoring of blood pressure and heart rate using a pressure transducer and a computer-based data acquisition system (Modular Instruments, Inc.). Two additional catheters were placed in the vena cava via the femoral veins (one in each vein) for administration of pentobarbital or either the endothein antagonist or the alpha 1a receptor antagonist. A supra-pubic incision is made approximately one-half inch lateral to the penis and the ureters, urinary bladder, prostate and urethra are exposed. The dome of the bladder is retracted to facilitate dissection of the ureters. The ureters are cannulated and then ligated, permitting urine to flow freely without filling the bladder. Umbilical tape is passed beneath the bladder neck and 1–2 cm distal to the prostate. The bladder dome is incised and a Millar microtip catheter transducer is advanced into the urethra. The neck of the bladder is ligated with the umbilical tape to to hold the transducer. The incision in the bladder dome is sutured with 3-0 silk. The transducer is withdrawn until the tip is in located in the prostatic urethra. The position of the catheter is verified by gently squeezing the prostate and noting the large increase in prostatic urethral pressure. The distal ligature is then tied.

Protocol:

Phenylephrine (10 ug/kg, ia) is administered and the pressor effect on intraurethral pressure (IUP) is measured. When blood pressure and IUP return to baseline, endothelin-1 (ET-1, 1 nmole/kg, ia) is administered and the increase in IUP is measured. When the blood pressure and IUP return to baseline (1 hour later), an efficacious dose of and endothelin antagonist or alpha-1a antagonist is administered. Ten to fifteen minutes later (when blood pressure has stabilized) the pressor responses to phenylephrine and ET-1 are measured again.

Results:

The results of the experiment will demonstrate that the endothelin antagonist will completely inhibit the IUP pressor response to ET-1 but not phenylephrine. The alpha-1a antagonist will inhibit the IUP pressor response to phenylephrine, but not to ET-1.

Conclusion:

The conclusion is that both ET-1 and phenyephrine can increase prostatic urethral tone independently and can be inhibited by an endothelin antagonist and alpha 1a antagonist, respectively. Therefore, if both ET-1 and alpha 1 adrenergic tone participate in prostatic urethral constriction in man (contributing to bladder outlet obstruction), then a combination therapy of an endothelin antagonist and alpha 1a antagonist will be more efficacious than either antagonist alone.

While the foregoing specification teaches the principles of the present invention, with examples provided for the purpose of illustration, it will be understood that the practice of the invention encompasses all of the usual variations, adaptations, modifications, deletions or additions of procedures and protocols described herein, as come within the scope of the following claims and its equivalents.

What is claimed is:

1. A composition comprising an alpha-1a adrenergic antagonist and an endothelin antagonist, wherein the alpha-1a adrenergic receptor antagonist is (4S)-trans-4-(3,4-difluorophenyl)-3-[1-(4-pyridin-2-yl-cyclohexyl)-(3R)-pyrrolidin-3-yl-carbamoyl]-6-methyl-2-oxo-1,2,3,4-tetrahydro-pyrimidine-5carboxylic acid methyl ester or a pharmaceutically acceptable salt thereof and the endothelin antagonist is a subtype non-selective antagonist which is Compound B

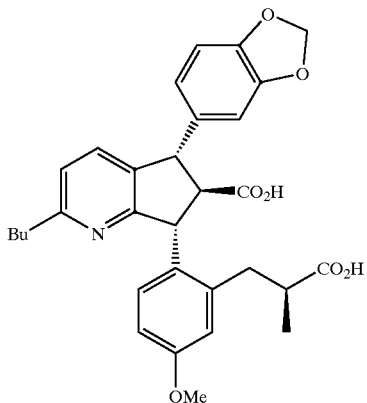

Compound B or a pharmaceutically acceptable salt thereof.

2. A method of treating benign prostatic hyperplasia in a subject in need thereof which comprises administering to the subject an effective amount of an alpha-1a antagonist, an endothelin antagonist, or pharmaceutically acceptable salts thereof, and optionally a 5alpha-reductase inhibitor, wherein the alpha-1a adrenergic receptor antagonist is (4S)-trans-4-(3,4-difluorophenyl)-3-[1-(4-pyridin-2-yl-cyclohexyl)-(3R)-pyrrolidin-3-ylcarbamoyl]-6-methyl- 2-oxo-1,2,3, 4tetrahydro-pyrimidine-5-carboxylic acid methyl ester or a pharmaceutically acceptable salt thereof and the endothelin antagonist is Compound B

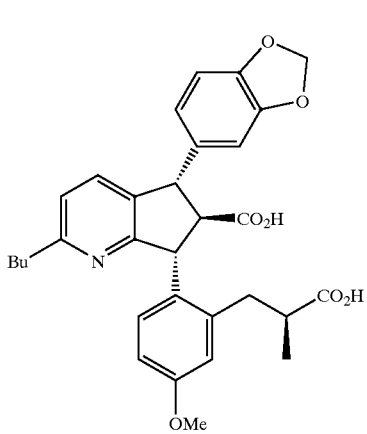

Compound B or a pharmaceutically acceptable salt thereof.

3. A method of relaxing lower urinary tract tissue in a subject in need thereof which comprises administering to the subject an effective amount of an alpha-1a antagonist, an endothelin antagonist, or pharmaceutically acceptable salts thereof, and optionally a 5alpha-reductase inhibitor, wherein the alpha-1a adrenergic receptor antagonist is (4S)-trans-4-(3,4-difluorophenyl)-3-[1-(4-pyridin-2-yl-cyclohexyl)-(3R)-pyrrolidin-3-ylcarbamoyl]-6-methyl-2-oxo-1,2,3,4-tetrahydro-pyrimidine-5-carboxylic acid methyl ester or a pharmaceutically acceptable salt thereof and the endothelin antagonist is Compound B

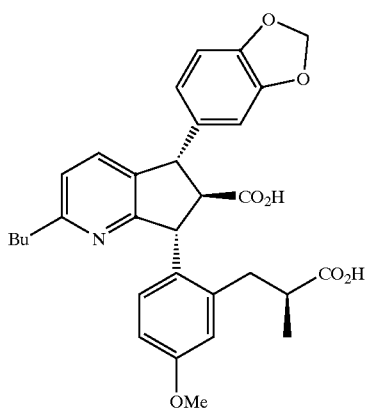

Compound B or a pharmaceutically acceptable salt thereof.

4. A method of improving lower urinary tract symptoms in a benign prostatic hyperplasia patient which comprises administering to the subject an effective amount of an alpha-1a antagonist, an endothelin antagonist, or pharmaceutically acceptable salts thereof, and optionally a 5alpha-reductase inhibitor, wherein the alpha-1a adrenergic receptor antagonist is (4S)-trans-4-(3,4-difluorophenyl)-3-[1-(4-pyridin-2-yl-cyclohexyl)-(3R)-pyrrolidin-3-ylcarbamoyl]-6-methyl-2-oxo-1,2,3,4-tetrahydro-pyrimidine-5-carboxylic acid methyl ester or a pharmaceutically acceptable salt thereof and the endothelin antagonist is Compound B Compound B

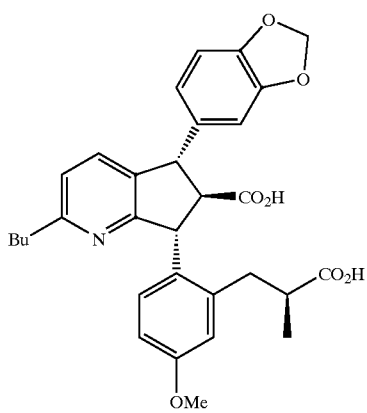

or a pharmaceutically acceptable salt thereof.

5. A pharmaceutical composition comprising an alpha-1a adrenergic receptor antagonist and an endothelin antagonist, or pharmaceutically acceptable salts thereof, and a pharmaceutically acceptable carrier, wherein the alpha-1a adrenergic receptor antagonist is (4S)-trans-4-(3,4-difluorophenyl)-3-[1-(4-pyridin-2-yl-cyclohexyl)-(3R)-pyrrolidin-3-ylcarbamoyl]-6-methyl-2-oxo-1,2,3,4-tetrahydro-pyrimidine-5-carboxylic acid methyl ester or a pharmaceutically acceptable salt thereof and the endothelin antagonist is Compound B, Compound B

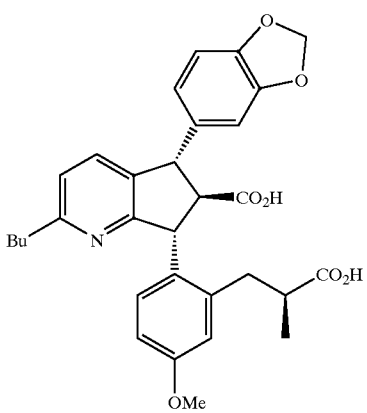

or a pharmaceutically acceptable salt thereof.

6. A pharmaceutical composition made by combining an alpha-1a adrenergic receptor antagonist, an endothelin antagonist, or pharmaceutically acceptable salts thereof, and a pharmaceutically acceptable carrier, wherein the alpha-1a adrenergic receptor antagonist is (4S)-trans-4-(3,4-difluorophenyl)-3-[1-(4-pyridin-2-yl-cyclohexyl)-(3R)-pyrrolidin-3-ylcarbamoyl]-6-methyl-2-oxo-1,2,3,4-tetrahydro-pyrimidine-5-carboxylic acid methyl ester or a pharmaceutically acceptable salt thereof and the endothelin antagonist is Compound B Compound B

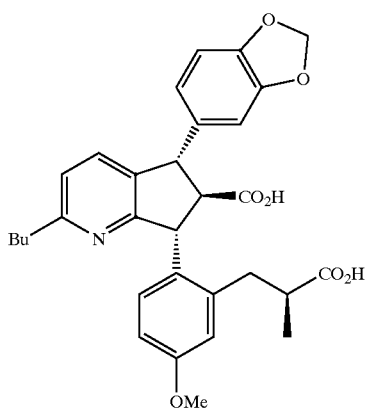

or a pharmaceutically acceptable salt thereof.

7. A process for making a pharmaceutical composition comprising combining an alpha-1a adrenergic antagonist, an endothelin antagonist, or pharmaceutically acceptable salts thereof, and a pharmaceutically acceptable carrier, wherein the alpha-1a adrenergic receptor antagonist is (4S)-trans-4-(3,4-difluorophenyl)-3-[1(4-pyridin-2-yl-cyclohexyl)3R)-pyrrolidin-3-ylcarbamoyl]-6-methyl-2-oxo-1,2,3,4-tetrahydro-pyrimidine-5-carboxylic acid methyl ester or a pharmaceutically acceptable salt thereof and the endothelin antagonist is Compound B Compound B

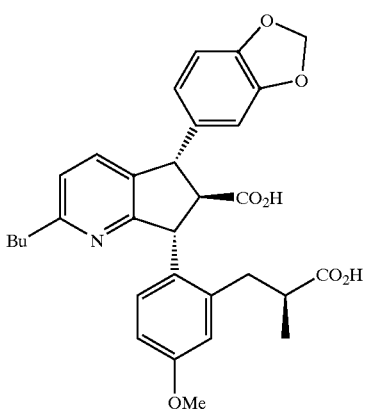

or a pharmaceutically acceptable salt thereof.

* * * * *